United States Patent
Van Stevendaal et al.

(10) Patent No.: US 7,580,499 B2
(45) Date of Patent: Aug. 25, 2009

(54) COHERENT-SCATTER COMPUTED TOMOGRAPHY

(75) Inventors: Udo Van Stevendaal, Ahrensburg (DE); Claas Bontus, Hamburg (DE); Peter Forthmann, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 271 days.

(21) Appl. No.: 10/575,584

(22) PCT Filed: Oct. 5, 2004

(86) PCT No.: PCT/IB2004/051968

§ 371 (c)(1),
(2), (4) Date: Apr. 11, 2006

(87) PCT Pub. No.: WO2005/036467

PCT Pub. Date: Apr. 21, 2005

(65) Prior Publication Data

US 2007/0140410 A1    Jun. 21, 2007

(30) Foreign Application Priority Data

Oct. 14, 2003    (EP) .................................. 03103798

(51) Int. Cl.
*A61B 6/03*    (2006.01)
(52) U.S. Cl. .................. 378/7; 378/4; 378/19; 378/87; 378/901
(58) Field of Classification Search ............... 378/4, 378/19, 210, 901
See application file for complete search history.

(56) References Cited

U.S. PATENT DOCUMENTS

| 475,172 | A | 5/1892 | Airey et al. |
| 6,470,067 | B1 * | 10/2002 | Harding ....................... 378/19 |
| 6,529,575 | B1 * | 3/2003 | Hsieh ........................... 378/4 |

OTHER PUBLICATIONS

Van Stevendaal et al., Filtered Back-Projection Reconstruction Technique for Coherent-Scatter Computed Tomography, May 15, 2003, Medical Imaging 2003: Image Processing, SPIE vol. 5032, pp. 1810-1819.*
Defrise et al., Improved 2D rebinning of helical cone-beam CT data using John's Equation, Nov. 2002, 2002 IEEE Nuclear Science Symposium Conference Record, vol. 3, pp. 1463-1469.*
Van Stevendaal et al., A reconstruction algorithm for coherent scatter computed tomography based on filtered back-projection, Aug. 22, 2003, Medical Physics, vol. 30, No. 9, pp. 2465-2474.*
Schlomka et al., Coherent Scatter Computed Tomography—A Novel Medical Imaging Technique, Jun. 5, 2003, Medical Imaging 2003: Physics of Medical Imaging, SPIE vol. 5030, pp. 256-265.*

* cited by examiner

*Primary Examiner*—Edward J Glick
*Assistant Examiner*—John M Corbett

(57) ABSTRACT

Known reconstruction techniques from coherent scattered x-rays apply non-exact reconstruction techniques. According to the present invention, a relatively wide spectrum of wave-vector transfers q of the scattered x-ray photons is acquired. The projection data is interpreted as line integrals in the x y-q space and the projection data is resorted to correspond to an acquisition along any source trajectory. Due to this, an exact helical reconstruction algorithms may be applied and redundant data may be used to obtain a better image quality.

15 Claims, 6 Drawing Sheets

COHERENT-SCATTER COMPUTED TOMOGRAPHY

The present invention relates to the field of coherent-scatter computed tomography (CSCT), where a fan-beam is applied to an object of interest. In particular, the present invention relates to a data processing device for performing a reconstruction of computed tomography data, to a computed tomography apparatus for examination of an object of interest, to a method of performing a reconstruction of computed tomography data and to a computer program for a data processor for performing a reconstruction of computed tomography data.

U.S. Pat. No. 4,751,722 describes a device based on the principle of registration of an angled distribution of coherent scattered radiation within angles of 1° to 12° as related to the direction of the beam. As set forth in the U.S. Pat. No. 4,751,722, the main fraction of elastic scattered radiation is concentrated within angles of less than 12°, and the scattered radiation has a characteristic angle dependency with well marked maxima, the positions of which are determined by the irradiated substance itself. As the distribution of the intensity of the coherently scattered radiation in small angles depends on molecular structure of the substance, different substances having equal absorption capacity (which cannot be differentiated with conventional transillumination or CT) can be distinguished according to the distribution of the intensity of the angled scattering of coherent radiation typical for each substance.

Due to the improved capabilities of such systems to distinguish different object materials, such systems find more and more application in medical or industrial fields.

The dominant component of low-angle scatter is coherent scatter. Because coherent scatter exhibits interference effects which depend on the atomic arrangement of the scattering sample, coherent-scatter computed tomography (CSCT) is in principle a sensitive technique for imaging spatial variations in the molecular structure of tissues across a 2D object section.

Harding et al. "Energy-dispersive x-ray diffraction tomography" Phys. Med. Biol., 1990, Vol. 35, No. 1, 33-41 describes a tomographic imaging technique based on an energy analysis at fixed angle, of coherent x-ray scatter excited in an object by polychromatic radiation. According to this method, a radiation beam is created by the use of suitable aperture systems, which has the form of a pencil and thus is also referred to as a pencil beam. Opposite to the pencil beam source, one detector element suitable for an energy analysis is arranged for detecting the pencil beam altered by the object of interest.

A coherent scatter set-up applying a fan-beam primary beam and a 2D detector in combination with CT was described in U.S. Pat. No. 6,470,067 B1. The shortcoming of the angle-dispersive set-up in combination with a polychromatic source are blurred scatter functions, which is described in e.g. Schneider et al. "Coherent Scatter Computed Tomography Applying a Fan-Beam Geometry" Proc. SPIE, 2001, Vol. 4320 754-763.

To become a competitive modality in the fields of medical imaging or non-destructive testing, the implemented reconstruction algorithm should assure both good image quality and short reconstruction times.

So far, the projection data acquired with fan-beam CSCT is reconstructed with the help for example, algebraic reconstruction techniques (ART), since ART has been shown to be highly versatile, for example, by J. A. Grant et al. "A reconstruction strategy suited to x-ray diffraction tomography", J. Opt. Soc. Am A12, 291-300 (1995). However, due to the computational complexity of such iterative reconstruction, such methods require a relatively long reconstruction time.

Furthermore, all known approaches apply a non-exact reconstruction technique.

It is an object of the present invention to provide for an improved reconstruction of tomography data.

According to exemplary embodiment of the present invention, the above object may be solved by a data processing device for performing a reconstruction of computed tomography data, wherein the computed tomography data is reconstructed from acquired CT (computed tomography) data, comprising at least a partial spectrum acquired by using a detector comprising energy resolving detector elements. Furthermore, a memory is provided for storing at least one of the acquired CT data and the computed tomography data. Also, a processor is provided, which is adapted to determine a wave-vector transfer by using the at least partial spectrum and to determine a reconstruction volume. A dimension of the reconstruction volume is determined by the wave-vector transfer. The wave-vector transfer represents curved lines in the reconstruction volume. Then, according to an aspect of the present invention, a rearranging of the CT data is performed, such that it corresponds to an acquisition along a desired source trajectory in the reconstruction volume.

Advantageously, the data processing device according to this exemplary embodiment of the present invention may perform a quasi-exact reconstruction technique for reconstruction data, such as an image, from read-outs of the detector. In this context, the term "reconstruction" is to be understood as covering steps or processes from the reading of the measured data from the detector to the display of the actually reconstructed data on, for example, a display or an output of information such as a material discrimination based on these read-outs.

The interpretation of the projection data as curved lines or line integrals in the reconstruction space and the appropriate resorting of the acquired CT data such that it corresponds to an acquisition, where the source of radiation used is displaced along a desired source trajectory, may allow for realizing exact helical reconstruction algorithms.

In other words, according to this exemplary embodiment of the present invention, the source of radiation may be displaced along a first trajectory, such as a circle, for data acquisition. Then, the data is rearranged such that it corresponds to data as if it had been acquired with a source of radiation displaced along a second trajectory which may be different to the first trajectory. The second trajectory may be a helix.

According to another exemplary embodiment of the present invention, the acquired CT data is acquired with a first source movement and the data is rearranged in the reconstruction volume such that it corresponds to data acquired with a second, different source movement. E.g. the first source movement may be a circle and the second source movement may be a helix. Due to this reordering or reorganization of the acquired CT data, the exact helical reconstruction algorithms, which are known in the art as described e.g. in Katsevich "Analysis of an exact inversion algorithm for spiral cone-beam CT", Phys. Med. Biol., vol. 47, p 2583-2597, 2002, which is hereby incorporated by reference, may be used for quasi-exactly reconstructing the data.

According to another exemplary embodiment of the present invention, a filtered back-projection is performed along the curved lines, which may be hyperbolas in the reconstruction volume.

According to another exemplary embodiment of the present invention, the three dimensions of the reconstruction volume are defined by the wave-vector transfer and by two linear independent vectors of the rotation plane of the source of radiation. Furthermore, the detector is a two-dimensional detector, which allows to achieve the full energy spectrum of the source of radiation, for example, of a polychromatic x-ray source. This yields a relatively wide spectrum of the wave-vector transfers of the scattered x-ray photons. Due to this, redundant data is acquired, which may be used to obtain a better image quality.

According to another exemplary embodiment of the present invention, the rearranging of the acquired CT data is performed by using John's equation. According to another exemplary embodiment of the present invention, a very simple linear equation is provided, which fulfills the data acquisition of a helical trajectory in the reconstruction volume, allowing for a fast and accurate and quasi-exact reconstruction of the computed tomography data.

According to another exemplary embodiment of the present invention, a computed tomography apparatus is provided, with a scatter radiation detector arranged at a detector unit opposite to an x-ray source, with an offset with respect to a slice plane of a fan-shaped x-ray beam generated by the x-ray source in a direction parallel to a rotational axis of the x-ray source and the scatter radiation detector. The scatter radiation detector comprises a plurality of energy resolving detector elements. According to an aspect of this exemplary embodiment of the present invention, a rearranging of the acquired CT data acquired by using the scatter radiation detector is performed such that it corresponds to an acquisition, where the x-ray source is displaced along a desired source trajectory in the reconstruction volume. In other words, the acquired CT data is rearranged as if it had been acquired by means of a desired movement of the scatter radiation detector and the x-ray source which may be different to the actual movement of the x-ray source during the data acquisition.

Advantageously, according to this exemplary embodiment of the present invention, a computed tomography apparatus is provided, which may perform a quasi-exact helical reconstruction of, for example, an x-ray image. Advantageously, this may allow for improved image quality and for a fast reconstruction.

According to another exemplary embodiment of the present invention, the scatter radiation detector is a two-dimensional detector, i.e. a 2D energy resolving detector, which may allow achieving the full energy spectrum of, for example, a polychromatic x-ray source. This may yield a relatively wide spectrum of the wave-vector transfers of the scattered x-ray photons. An interpretation of the projection data as line integrals in the reconstruction volume and the resorting of the data as if it had been taken along the helical source trajectory may allow for applying exact helical reconstruction algorithms. Furthermore, redundant data may be used to obtain a better image quality.

According to another exemplary embodiment of the present invention, a method of performing a reconstruction of computed tomography data is provided, comprising a rearranging of acquired CT data, acquired by means of an energy resolving detector, which may be a two-dimensional energy resolving detector, as if it had been taken by an acquisition along a helical source trajectory.

Advantageously, according to this exemplary embodiment of the present invention, a very fast and efficient method may be provided, allowing for an exact reconstruction of the data, which may allow for an improved image quality.

According to another exemplary embodiment of the present invention, a computer program for a data processor for performing a reconstruction of computed tomography data is provided. The computer program according to the present invention is preferably loaded into a working memory of the data processor. The data processor is thus equipped to carry out the method of the invention. The computer program may be stored on a computer readable medium, such as a CD-ROM. The computer program may also be presented over a network such as the WorldWideWeb, and can be downloaded into the working memory of a data processor from such a network.

It may be seen as the gist of an exemplary embodiment of the present invention that a resorting or extrapolation of the data acquired during a circular acquisition (i.e. the data read-outs from, for example, a two-dimensional energy resolving detector) is performed, such that the data corresponds to an acquisition along a different source trajectory as actually used for acquisition in the x-y-q space, or the reconstruction volume. In other words, e.g. data acquired during a circular acquisition is resorted and/or extrapolated such that it represents data in an x-y-q space, as if it had been taken by an acquisition with a helical source trajectory. Advantageously, this may allow for a quasi-exact helical reconstruction, since known reconstruction algorithms adapted to helical source trajectories may be used. Furthermore, according to an aspect of the present invention, a two-dimensional energy resolving detector may be used, allowing to achieve a full energy spectrum of the source of radiation, which yields a relatively wide spectrum of the wave-vector transfers of the scattered photons. Advantageously, this may allow for an improved image quality and for an improved data reconstruction.

These and other aspects of the present invention will become apparent from and elucidated with reference to the embodiments described hereinafter.

Exemplary embodiments of the present invention will be described in the following, with reference to the following drawings.

Figure 1:
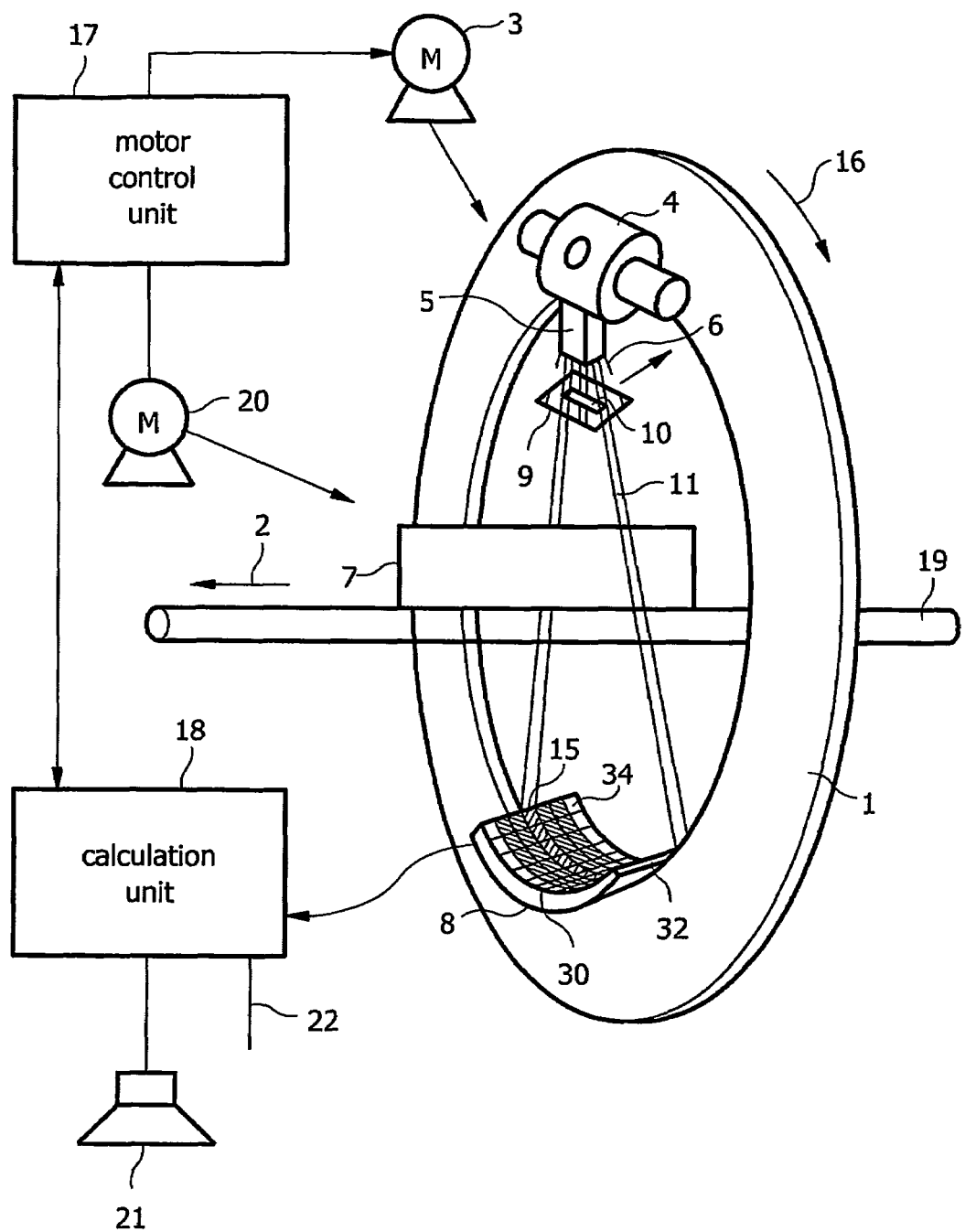
FIG. 1 shows a schematic representation of an exemplary embodiment of a CSCT scanner according to the present invention.

FIG. 1 shows an exemplary embodiment of a computer tomograph according to the present invention. With reference to this exemplary embodiment, the present invention will be described for the application in baggage inspection to detect hazardous materials such as explosives in items of baggage. However, it has to be noted that the present invention is not limited to applications in the field of baggage inspection, but can also be used in other industrial or medical applications, such as for example in bone imaging or a discrimination of tissue types in medical applications.

The apparatus depicted in FIG. 1 is a fan-beam CSCT scanner, which allows in combination with an energy-resolving detector and with tomographic reconstruction a good spectral resolution, even with a polychromatic primary fan-beam. The CSCT scanner depicted in FIG. 1 comprises a gantry 1, which is rotatable around a rotational axis 2. The gantry 1 is driven by means of a motor 3. Reference character 4 designates a source of radiation, such as an x-ray source, which, according to and aspect of the present invention, emits a polychromatic radiation.

Reference character 5 designates a first aperture system, which forms the radiation beam emitted from the radiation source 4 to a cone shaped radiation beam 6. Furthermore, there is provided another aperture system 9 consisting of a diaphragm or a slit collimator. The aperture system 9 has the form of a slit 10, such that the radiation emitted from the source of radiation 4 is formed into a fan-beam 11. According to a variant of this exemplary embodiment of the present invention, the first aperture system 5 may also be omitted and only the second aperture system 9 may be provided.

The fan-beam 11 is directed such that it penetrates the item of baggage 7, arranged in the center of the gantry 1, i.e. in an examination region of the CSCT scanner and impinges onto the detector 8. As may be taken from FIG. 1, the detector 8 is arranged on the gantry 1 opposite to the radiation source 4, such that the slice plane of the fan-beam 11 intersects a row or line 15 of the detector 8. The detector 8 depicted in FIG. 1 has seven detector lines, each comprising a plurality of detector elements. As mentioned above, the detector 8 is arranged such that the primary radiation detector 15, i.e. the middle line of the detector 8 is in the slice plane of the fan-beam 11.

As can be taken from FIG. 1, the detector 8 comprises two types of radiation detector lines: a first type of detector lines 30 and 34, which are indicated without hatching in FIG. 1, which are detector lines consisting of energy resolving detector cells. According to an aspect of the present invention, these first detector elements (lines 30 and 34) are energy-resolving detector elements. Preferably, the energy resolving detector elements are direct-converting semiconductor detectors. Direct-converting semiconductor detectors directly convert the radiation into electrical charges—without scintillation. Preferably, these direct-converting semiconductor detectors have an energy resolution better than 10% FWHM, i.e. $\Delta E/E<0.1$, with $\Delta E$ being the full-width at half maximum (FWHM) of the energy resolution of the detector.

Such detector cells of lines 30 and 34 may be cadmiumtelluride or CdZnTe (CZT) based detector cells, which are both outside of the slice plane of the fan-beam 11. In other words, both energy resolving lines 30 and 34 are arranged at the gantry 1 opposite to the x-ray source 4 with an offset from the slice plane in a direction parallel to the rotational axis 2. The detector line 30 is arranged with a positive offset with respect to the direction of the rotational axis 2 depicted in FIG. 1, whereas the line 34 is arranged with a negative offset from the slice plane with respect to the direction of the rotational axis 2 depicted in FIG. 1.

The detector lines 30 and 34 are arranged at the gantry 1 such that they are parallel to the slice plane and out of the slice plane with an offset in a positive or negative direction of the rotational axis 2 of the gantry 1, such that they receive or measure a scatter radiation scattered from the item of baggage 7 in the examination area of the CSCT scanner. Thus, in the following, lines 30 and 34 will also be referred to as scatter radiation detector. It has to be noted that according to a preferred embodiment of the present invention, the energy resolving lines 30 and 34 form a two dimensional energy resolving scatter radiation detector. In other words, preferably, a plurality of energy resolving lines 30 and 34 are arranged on both sides of the line 15. Thus, a detector 8, having only a non energy resolving line 15 in the slice plane and having energy resolving lines arranged spaced from the slice plane, may be advantageous. Thus, if, in the following the term "scatter radiation detector" is used, it includes any detector with at least two lines of energy resolving detector cells, which are arranged out of the fan plane of the fan-beam 11, such that it receives photons scattered from the item of baggage 7.

The second type of detector lines provided on the detector 8, which are indicated by a hatching, are scintillator cells. In particular, line 15 is arranged such that it is in the slice plane of the fan-beam 11 and measures the attenuation of the radiation emitted by the source of radiation 4, caused by the item of baggage 7 in the examination area. As depicted in FIG. 1, right and left of the line 15, there may be provided further detector lines including scintillator detector cells. However, as indicated above, there may be only one detector line with scintillator cells, namely the line 15 in the slice plane, and the remaining lines of the detector 8 may be energy resolving lines. By this, a two dimensional energy resolving detector (such a scatter radiation detector) may be provided.

As already indicated with respect to the energy resolving lines 30 and 34, the provision of only the line 15 measuring the attenuation caused by the item of baggage 7 of the primary beam of the fan-beam 11 in the slice plane may be sufficient. However, as in the case of the energy resolving lines 30 and 34, a provision of a plurality of detector lines 32, each comprising a plurality of scintillator cells, may further increase the measurement speed of the CSCT scanner. In the following, the term "primary radiation detector" will be used to refer to a detector, including at least one line of scintillator or similar detector cells for measuring an attenuation of the primary radiation of the fan-beam 11.

According to a preferred embodiment of the present invention, a plurality of energy resolving lines 30 and 34 are provided, such that a two-dimensional energy resolving detector is provided. This may allow to gather additional, redundant data, which may be used later on for improving the image quality. Furthermore, this may allow to reduce a scanning time.

With one energy-resolving line, only a fraction of the full spectrum for wave-vector transfers may be obtained. In addition, the spectrum may have a lower boundary, caused by a distance of the detector line to the slice plane or scan plane. Thus, using a 2D (two dimensional) detector may lead to a wider spectrum of the wave-vector transfers. In particular, the lower boundary may be shifted to relatively small values. Furthermore, a 2D detector may allow to yield redundant data. By pre-processing this data in accordance with an aspect of an exemplary embodiment of the present invention, it can be used as input for an exact reconstruction technique.

As may be taken from FIG. 1, the detector cells of the detector 8 are arranged in lines and columns, wherein the columns are parallel to the rotational axis 2, whereas the lines are arranged in planes perpendicular to the rotational axis 2 and parallel to the slice plane of the fan-beam 11.

The apertures of the aperture systems 5 and 9 are adapted to the dimensions of the detector 8 such that the scanned area of the item of baggage 7 is within the fan-beam 11 and that the detector 8 covers the complete scanning area. Advantageously, this allows to avoid unnecessary excess radiation applied to the item of baggage 7. During a scan of the item of baggage 7, the radiation source 4, the aperture systems 5 and 9 and the detector 8 are rotated along the gantry 1 in the direction indicated with arrow 16. For rotation of the gantry 1 with the source of radiation 4, the aperture systems 5 and 9 and the detector 15, the motor 3 is connected to a motor control unit 17, which is connected to a calculation unit 18.

In FIG. 1, the item of baggage 7 is disposed on a conveyor belt 19. According to an exemplary embodiment of the present invention, as mentioned above, a circular data acquisition is performed where the x-ray source 4 is displaced along a circular source trajectory, i.e. is rotated in a rotational plane around the rotation axis without a movement of the item of baggage 7. Thus, the conveyor belt 19 is operated such that the item of baggage is immobile when the x-ray source 4 performs a circular movement (i.e. a circular acquisition) around the item of baggage 7 allowing for a sufficient data acquisition. Then, the item of baggage 7 is moved by e.g. a preset increment, and then another scan of another slice of the item of baggage 7 is performed during which the conveyor belt 19 is not operated.

The detector 8 is connected to a calculation unit 18. The calculation unit 18 receives the detection results, i.e. the readouts from the detector elements of the detector 8 and determines a scanning result on the basis of the scanning results from the detector 8, i.e. from the energy resolving lines 30 and 34 and the lines 15 and 32 for measuring the attenuation of the primary radiation of the fan-beam 11. In addition to that, the calculation unit 18 communicates with the motor control unit 17 in order to coordinate the movement of the gantry 1 with the motors 3 and 20 or with the conveyor belt 19.

The calculation unit 18 is adapted for reconstructing an image from readouts of the primary radiation detector, i.e. detector lines 15 and 32 and the scatter radiation detector, i.e. lines 30 and 34. The image generated by the calculation unit 18 may be output to a display (not shown in FIG. 1) via an interface 22.

The calculation unit, which may be realized by a data processor, may be adapted to perform a filtered back-projection on the read-outs from the detector element of the detector 8, i.e. from the read-outs from the energy resolving lines 30 and 34 and the lines 15 and 32 for measuring the attenuation of the primary radiation of the fan-beam 11. The back-projection performed in the calculation unit 18, which forms part of the image reconstruction will be described in further detail with reference to FIG. 7.

Furthermore, the calculation unit 18 may be adapted for the detection of explosives in the item of baggage 7 on the basis of the readouts of the lines 30 and 34 and 15 and 32. This can be made automatically by reconstructing scatter functions from the readouts of these detector lines and comparing them to tables including characteristic measurement values of explosives determined during preceding measurements. In case the calculation unit 18 determines that the measurement values read out from the detector 8 match with characteristic measurement values of an explosive, the calculation unit 18 automatically outputs an alarm via a loudspeaker 21.

In particular, the calculation unit 18 may by adapted to perform a determination of the wave-vector transfer by using at least a partial spectrum acquired from the read-outs from the detector 8 and, in particular, from the read-outs of the energy resolving lines 30 and 34. As may be taken from FIG. 1, the data is acquired during a circular acquisition, referring to the source trajectory in the x-y-z space Then, the measured data is interpreted as line integrals in the x-y-q space, where q is the wave-vector transfer and x and y are linear independent vectors in the rotation plane of the source of radiation 4. Then, the measured data is resorted and extrapolated, such that it corresponds to an acquisition along a helical trajectory in the x-y-q space, i.e. it is reordered to be as if it had been taken along a helical source trajectory. Then, the data may be pre-processed in order to allow that the data is applied to conventional helical reconstruction algorithms, for example, the reconstruction technique described by Katsevich "Analysis of an exact inversion algorithm for spiral cone-beam CT", Phys. Med. Biol., vol. 47, p. 2583-2597, 2002, which is hereby incorporated by reference. Finally, the data is back-projected. This back-projection may be performed along the curved lines, such as hyperbolas in the x-y-q space of the wave-vector transfer. This operation will be described in further detail with reference to FIG. 6.

During the subsequent description of FIGS. 2 to 5, the same reference numbers as used in FIG. 1 will be used for the same or corresponding elements.

Figure 2:
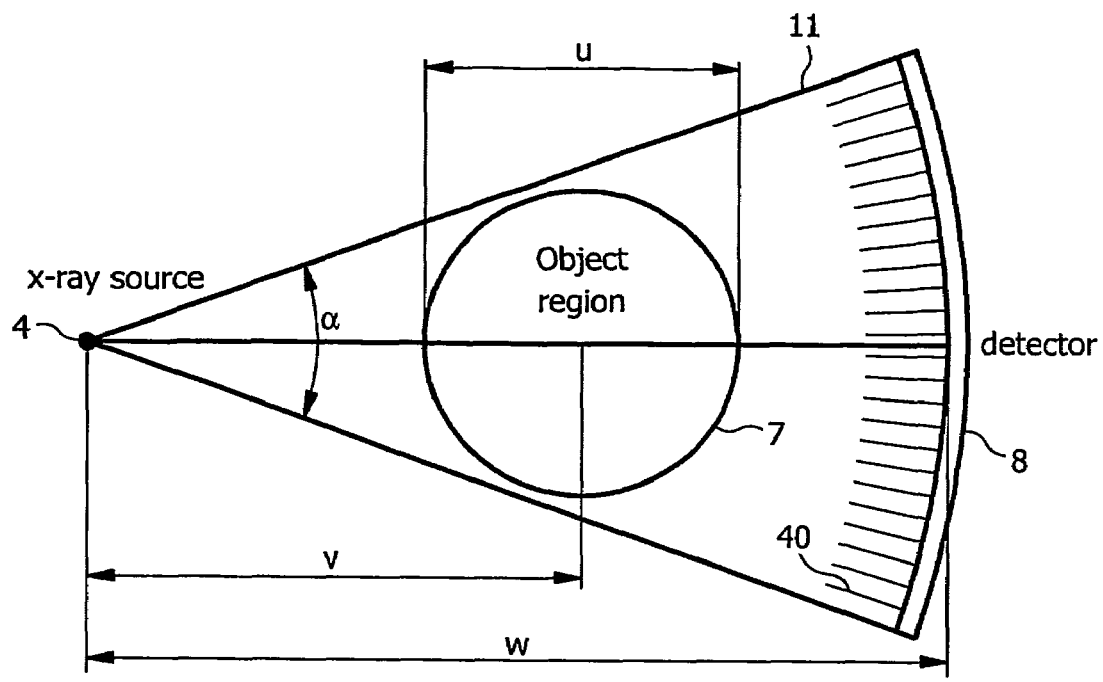
FIG. 2 shows a schematic representation of the geometry of the CSCT scanner of FIG. 1 for the measurement of coherent scatter radiation.

FIG. 2 shows a simplified schematic representation of a geometry of the CSCT scanning system depicted in FIG. 1. As may be taken from FIG. 2, the x-ray source 4 emits the fan-beam 11 such that it includes the item of baggage 7 in this case having a diameter of u and covers the entire detector 8. The diameter of the object region may, for example, be 100 cm. In this case, an angle α of the fan-beam 11 may be 80°. In such an arrangement, a distance v from the x-ray source 4 to the center of the object region is approximately 80 cm and the distance of the detector 8, i.e. of the individual detector cells from the x-ray source 4 is approximately w=150 cm.

As can be taken from FIG. 2, according to an aspect of the present invention, the detector cells or lines can be provided with collimators 40 to avoid that the cells or lines measure unwanted radiation having a different scatter angle. The collimators 40 have the form of blades or lamellas, which can be focused towards the source. The spacing of the lamellas can be chosen independently from the spacing of the detector elements.

Instead of a bent detector 8 as depicted in FIGS. 1 and 2, it is also possible to use a flat detector array.

Figure 3:
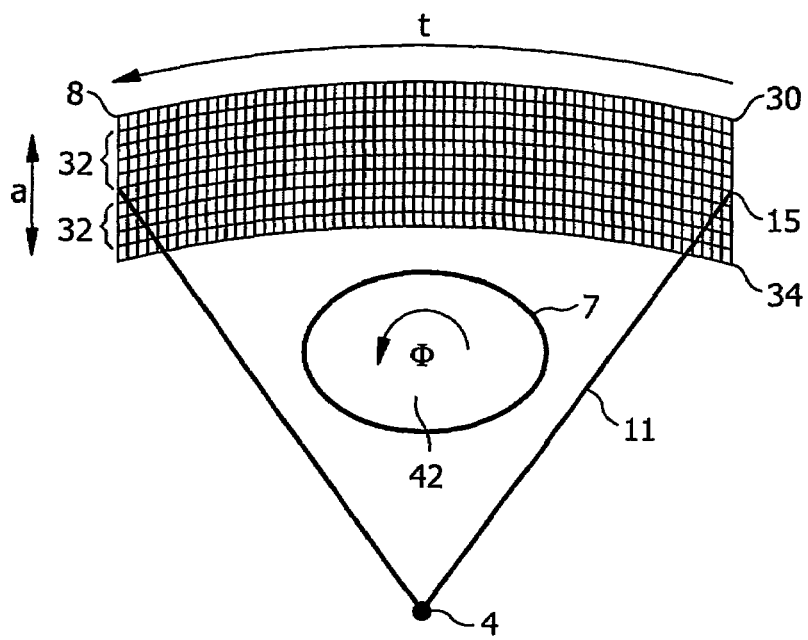
FIG. 3 shows another schematic representation of the geometry of the CSCT scanner of FIG. 1.

FIG. 3 shows another schematic representation of a detector geometry as used in the CSCT scanner of FIG. 1. As already described with reference to FIG. 1, the detector 8 may comprise one, two or more energy resolving detector lines 30 and 34 and a plurality of lines 15 and 32 for measuring the attenuation of the primary fan-beam caused by the item of baggage 7. As may be taken from FIG. 3, preferably the detector 8 is arranged such that one line of the lines 15 and 32, preferably the middle line 15 of the detector 8, is within the slice plane of the fan-beam 11 and thereby measures the attenuation in the primary radiation. As indicated by arrow 42, the x-ray source 4 and the detector 8 are rotated together around the item of baggage in the rotation plane to acquire projections from different angles to perform a circular acquisition.

As depicted in FIG. 3, the detector 8 comprises a plurality of columns t.

Figure 4:
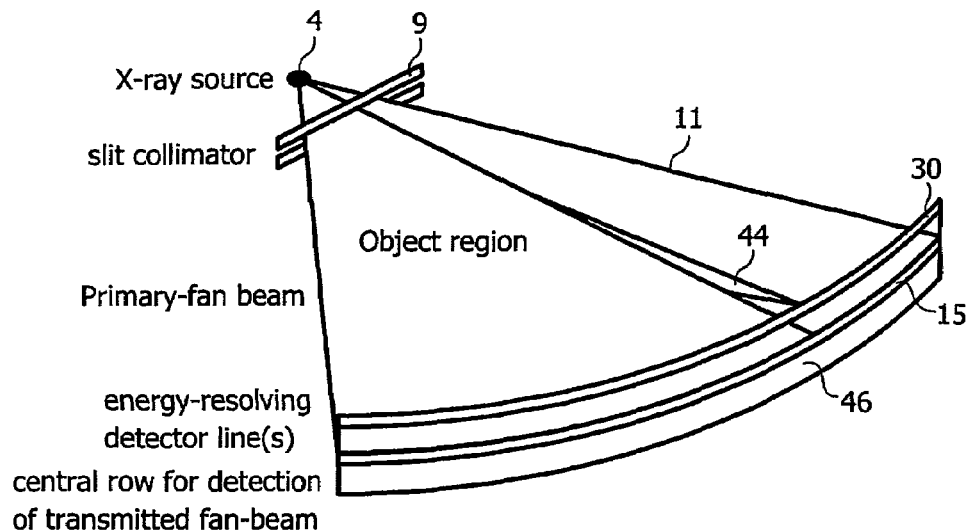
FIG. 4 shows another schematic representation of the measurement geometry of the CSCT scanner of FIG. 1 for further explaining the present invention.

FIG. 4 shows another schematic representation of the geometry of the CSCT scanner depicted in FIG. 1 for further explaining the present invention. In FIG. 4, a detector 46 is depicted, comprising only one line 15 and only one line 30. The line 15 is arranged in the slice plane of the fan-beam 11 formed by the aperture system 9, which in this case is a slit collimator and generated by means of the source of radiation or x-ray source 4. The line 15 comprises, for example, scintillator cells or other suitable cells for measuring the attenuation of the primary beam of the fan-beam 11 and allows for an integral measurement of the attenuation of the primary fan-beam caused by the object of interest in the object region or examination region.

Line 30 depicted in FIG. 4 includes energy resolving cells. As may be taken from FIG. 4, the line 30 is arranged parallel to the slice plane of the fan-beam 11 but out of the plane. In other words, the line 30 is arranged in a plane parallel to the slice plane and parallel to the line 15.

Reference numeral 44 indicates a scatter radiation, i.e. a photon scattered by the object of interest, such as the item of baggage. As may be taken from FIG. 4, the scatter radiation leaves the slice plane and impinges onto a detector cell of the line 30.

Figure 5:
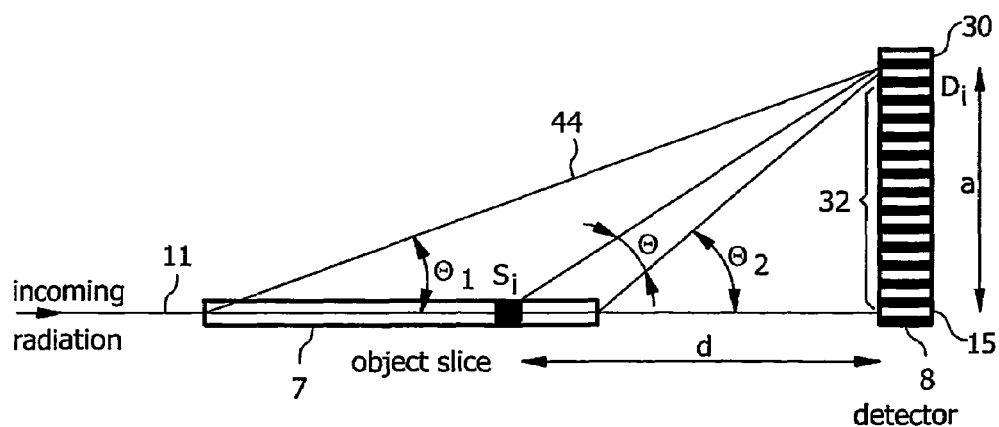
FIG. 5 shows a schematic representation of a side view of the geometry of the CSCT scanner of FIG. 1.

FIG. 5 shows a side view of the detector geometry of the CSCT scanner of FIG. 1. FIG. 5 can also be contemplated as showing a side view of FIG. 4, where, however, instead only the provision of one line 30 and one line 15, in FIG. 5, there is provided a plurality of detector lines 32 between the line 30 and the line 15. The detector element $D_i$ of the line 30 is an energy resolving detector element. The detector element $D_i$ is arranged with a fixed distance a from the slice plane of the primary fan-beam. According to an aspect of the present invention, for each detector element $D_i$ of the column t and for each projection $\Phi$ (see FIG. 3) an intensity spectrum I (E, t, $\Phi$) is measured. Performing this measurement for a plurality of projections $\Phi$ along a circular scan path, a three-dimensional dataset is acquired. Each object pixel is described by three coordinates (x, y, q). Thus, according to an aspect of the present invention, for reconstructing an image or for reconstructing further information from the three-dimensional dataset, a 3D→3D reconstruction method can be used.

Figure 6:
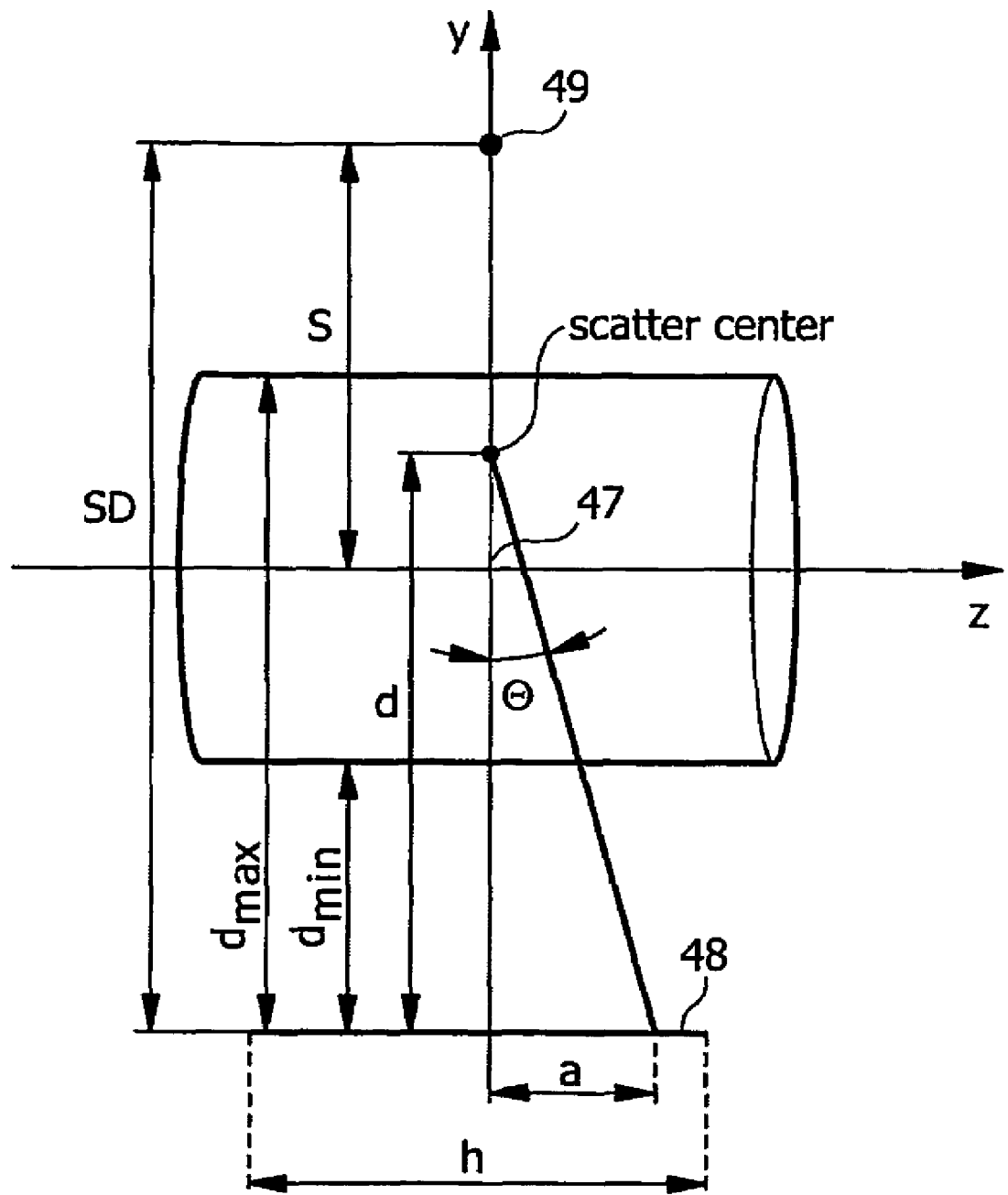
FIG. 6 shows a schematic representation of a multi-line CSCT scanner according to another exemplary embodiment of the present invention.

FIG. 6 shows a schematic drawing of an exemplary embodiment of a multi-line CSCT scanner. This scanner is provided with a detector 48, comprising a plurality of lines of energy resolving detector elements, which may be the same as the ones described with reference to FIG. 1. The source of radiation 49 is provided with collimator means, such that it generates a fan-beam of x-rays. The arrangement of the detector 48 and the source of radiation 49 is such that the detector 48 is focus centered. The view depicted in FIG. 6 is parallel to the scanned plane or slice plane in order to further clarify the scanning process out of the x-y plane, i.e. the rotation plane of the source of radiation 49 and the detector 48. As may be taken from FIG. 6, a distance between the source of radiation 49 and the detector 48 is indicated as "SD"; a distance between the source 49 and the center of rotation 47 is indicated by S, a distance between the scatter center and the detector 48 is indicated by d, a distance between a detector element receiving radiation and the scanned plane or sliced plane is given by a and h indicates a height of the detector 48.

The z coordinate axis is a normal on the center of the rotation plane of the source of radiation 49, i.e. the axis of rotation of the source of radiation 49. They coordinate is in the rotation plane of the source of radiation.

As may be taken from FIG. 6, for the following description, a CSCT scanner with, for example, a polychromatic x-ray source 49 and a D detector 49 is considered. The detector comprises or consists of energy resolving detector elements, which may be similar to the ones described with reference to FIG. 1. The emitted x-rays have been collimated, such that a fan-beam radiates the object of interest located in an area around the center of radiation 47.

According to an exemplary embodiment of the present invention, the following method of operation may be applied in the above scanner, or in the scanner described with reference to FIG. 1, for reconstructing the CSCT data, i.e. for reconstructing an image from the read-outs of the detectors 8 and 48.

Step 1: The data is measured during a circular acquisition referring to the source trajectory in the x-y-z space. In other words, read-outs are gathered from detectors 8 or 48, while the source of radiations 4 and 49 and the detectors 8 and 48 are rotated around the object of interest in a rotational plane. The read-outs are referred to as measured data or acquired CSCT data. The measured CSCT data are interpreted as line integrals in the x-y-q space, where q represents the wave-vector transfers. The calculation of the wave-vector transfers will be described later on.

Step 2: The acquired CSCT data is resorted and extrapolated, such that it corresponds to an acquisition along a helical trajectory in the x-y-q space.

Step 3: A further step may be performed in order to preprocess the data according to conventional helical reconstruction algorithms, such as, for example, the exact reconstruction technique described by Katsevich "Analysis of an exact inversion algorithm for spiral cone-beam CT", Phys. Med. Biol., vol. 47, p. 2583-2597, 2002, which is hereby incorporated by reference.

Step 4: Then, the resorted and/or extrapolated data may be back projected. This back-projection may be performed along the curved lines in the x-y-q space. These curved lines may, for example, be hyperbolas.

This operation, in particular step 2, will be described in more detail in the following:

CSCT makes use of coherently scattered x-rays, in order to reconstruct the coherent scatter form factor $F^2(q)$. The differential cross-section for coherently scattered x-rays $d\sigma_{Rayleigh}/d\Omega$ is given by $$\frac{d\sigma_{Raleigh}}{d\Omega} = \frac{1}{2}r_e^2(1 + \cos^2\Theta)F^2(q), \qquad (1)$$

where $r_e$ denotes the classical electron radius, and $\Theta$ the angle between the incoming and the scattered x-rays. The wave-vector transfer q causing the deviation of the photon by the angle $\Theta$ is defined by $$q = \frac{E}{hc}\sin(\Theta/2), \qquad (2)$$

with the energy E of the corresponding x-ray photon, Planck's constant h and the speed of light c. For scattering under small angles, e.g. the angle regime of interest here is between 0 and 5°, $\sin(\Theta/2)$ can be approximated by $\Theta/2$, and Eq. (2) can be written as $$q \approx \frac{E}{hc}\frac{\Theta}{2}. \qquad (3)$$

According to FIG. 6, the scatter angle is given by the distance d of the scatter center from the detector and the distance a of the detector element which receives the scattered radiation from the scanning plane:

$$\tan\Theta \approx \Theta = \frac{a}{d}. \qquad (4)$$

Together with Eq. (3), this yields:

$$q = \frac{E}{hc}\frac{a}{2d}. \quad (5)$$

The x-y-q space, Eq. (5) describes hyperbolas. These hyperbolas can be approximated by straight lines. Among several possibilities is, for example, an approximation such that the area under a straight line matches the area of the corresponding hyperbola. Another approximation is described here. The straight line intersects the hyperbola at the beginning ($d_{max}$) and at the end ($d_{min}$) of the region of interest:

$$q = \frac{1}{2hc}\left[\frac{d_{min} + d_{max} - d}{d_{min} \times d_{max}}\right]aE. \quad (6)$$

A scanning system is considered, such as the ones depicted in FIGS. 1 and 6, where the real path can be resorted and extrapolated such that they correspond to an acquisition along a helical trajectory in the x-y-q space. The extrapolation of the data measured on a circular trajectory to virtual neighboring trajectories is done by using John's Equation. The idea of John's Equation is that the space of line integrals through 3D space is 4D, thus the mapping from object function to its line integral function creates an additional dimension, as described in S. K. Patch, "Consistency conditions upon 3D CT data and the wave equation", Phys. Med. Biol. 47, 2637-2650. U.S. Pat. No. 6,173,030 (1999), which is hereby incorporated by reference.

Figure 7A:
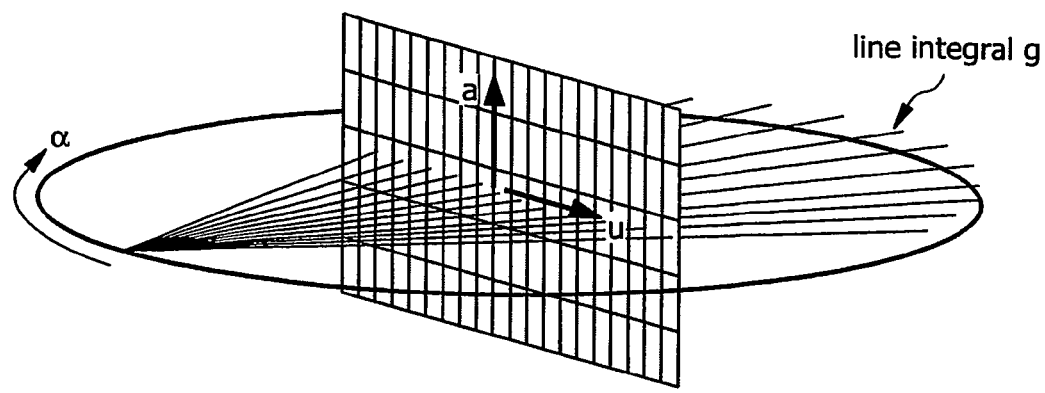
FIGS. 7a and 7b are schematic drawings to explain the idea of John's equation.
Figure 7B:
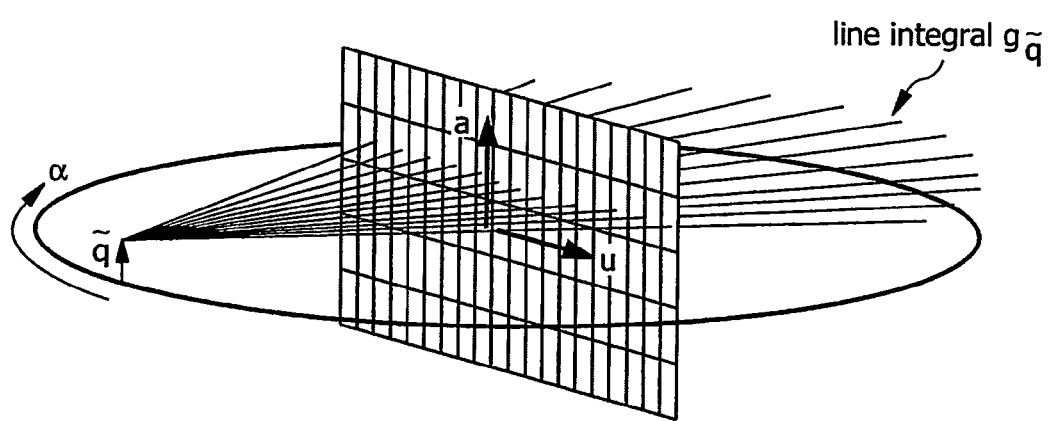

FIGS. 7a and 7b are schematic drawings in order to further explain the idea of John's Equation. The line integrals in FIG. 7b for the virtual source position $\tilde{q}$ are extrapolated from the line integrals measured for source positions for $\tilde{q}=0$ shown in FIG. 7a.

This implies redundancy in line integral space, which is then used to construct unmeasured from measured data as described in S. K. Patch "Computation of unmeasured third-generation VCT views from measured views", IEEE Trans. Med. Img. MI-21, 801-813. U.S. Pat. No. 6,292,526 (1999), which is hereby incorporated by reference. John's Equation is parametrized as follows for our set of geometry parameters, as described in M. Defrise, F. Noo, H. Kudo, "Improved 2D rebinning of helical cone-beam CT data using John's equation", Proc. 2002 IEEE Nuclear Science and Medical Imaging Symposium, Norfolk (Va.), Paper M10-74, which is hereby incorporated by reference:

$$R^2 g_{uq} - 2ug_a - (R^2 + u^2)g_{ua} - Rg_{\alpha a} - ua g_{aa} = 0, \quad (7)$$

where R is the distance from the virtual source position to the iso-center and u is the distance from the central ray to the exposed detector column in fan direction. The line integrals are denoted by g and the derivative of the line integral with respect to a variable is expressed by the index. From the measured line integrals g, the line integrals $g_q$ can be extrapolated for a virtual source position $\tilde{g}$ according to $$g(u,a,\alpha,\tilde{q}) = g(u,a,\alpha,0) + \Delta \tilde{q} g_q(u,a,\alpha,0). \quad (8)$$

Therefore, Eq. (7) has to be solved for $\tilde{q}$. Reforming of Eq. (7) to $$g_{u\tilde{q}} = \frac{2u}{R^2}g_a + \frac{(R^2+u^2)}{R^2}g_{ua} + \frac{1}{R}g_{\alpha a} + \frac{ua}{R^2}g_{aa}, \quad (9)$$

and partial integration with respect to u leads to $$g_{\tilde{q}} = \frac{(R^2+u^2)}{R^2}g_{a} + \frac{1}{R}\int\left(g_{\alpha a} + \frac{ua}{R}g_{aa}\right)da, \quad (10)$$

which are the line integrals for the virtual source position $\tilde{q}$.

The acquired and extrapolated data can now be resorted such that they correspond to an acquisition along a helical trajectory in the x-y-q space. Let $\vec{R}$ be the vector from the center of rotation of the scanning system to the virtual source. The helical trajectory results in:

$$\vec{R}(\alpha) = R\begin{pmatrix}\cos\alpha\\ \sin\alpha\\ k\alpha\end{pmatrix} = R\begin{pmatrix}\cos\alpha\\ \sin\alpha\\ \tilde{q}\end{pmatrix}, \quad (11)$$

where α denotes the angular source position in relation to the x-axis.

In a certain range, each value of $q\epsilon[q_{min},q_{max}]$ can be expressed by the linear equation $$q = \tilde{q} + \frac{1}{2hc}\left[\frac{d_{min} + d_{max} - d}{d_{min} \times d_{max}}\right]aE, \quad (12)$$

which fulfils the data acquisition of a helical trajectory in the x-y-q space. By this description, it is possible to define an offset $\alpha_0$ as a starting point for the helical data acquisition, in order to use redundant data for the reconstruction process. This may lead to better image quality.

The above described steps 1 to 4, in particular Step 3 may be applied and implemented in the CSCT scanner depicted and described with reference to FIGS. 1 to 5, in the scanner depicted in FIG. 6 and in the data processing device depicted in FIG. 9.

Figure 8:
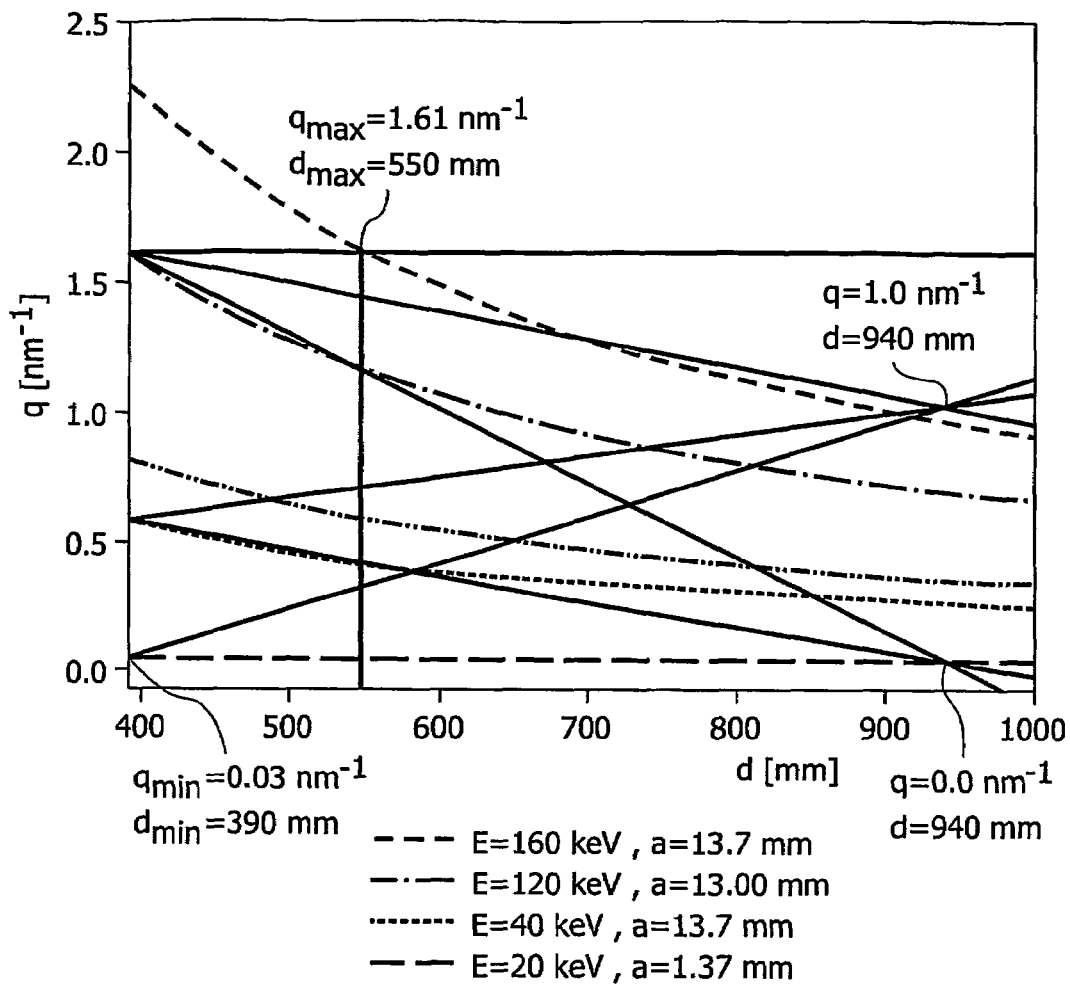
FIG. 8 shows characteristics of the wave-vector transfer q in dependence on the distance D between the scatter center and the detector for further explaining the present invention.

FIG. 8 shows an example for the characteristics of the wave-vector transfer q in dependence of the distance d of the scatter center from the detector. The distance S of the source to the center of rotation is chosen to be 570 mm, and the distance of the detector to the center of rotation is 470 mm, respectively. The distance R of the virtual source to the center or rotation is chosen to be 470 mm. The detector is supposed to consist of 20 rows of energy-resolving element with a size of 0.75×0.75 mm² in center of rotation. The x-ray source yields a spectrum of energies between 20 and 160 keV. The object of 160 mm in diameter is placed in the center of rotation. The range of allowed q-values is defined by the object size, the detector dimension and the energy spectrum. In the given example, $q\epsilon[0.03, 1.61]$, and all q values can be described by Eq. (12). The straight lines for the virtual source position at q=1.0 nm$^{-1}$ are obtained by extrapolation according to Eq. 8.

As may be taken from FIG. 8, characteristics of the wave-vector transfer in dependence of the distance d between the scatter center and the detector are depicted. For a given energy E, a certain detector element with a distance a to the scan plane or slice plane receives radiation from the scatter centers arranged along a ray through the object under q-values being described by the hyperbolas. The straight lines are approximations to the corresponding hyperbola. In the range between $q_{min}$ and $q_{max}$ determined by E, h and the object diameter, every value for the wave-vector transfer may be expressed by equation (12). The straight lines intersect at the virtual source position R.

Figure 9:
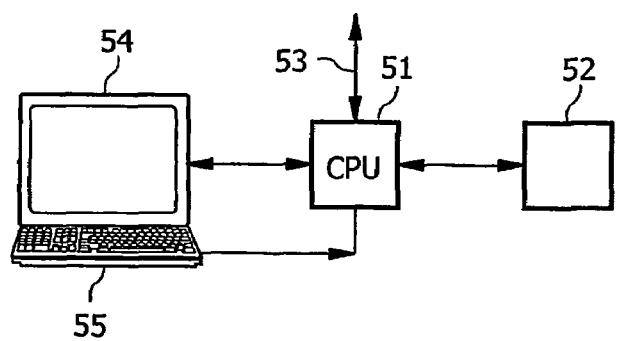
FIG. 9 shows a simplified schematic representation of an exemplary embodiment of a data processing device according to the present invention.

FIG. 9 shows an exemplary embodiment of a data processing device for performing steps 1 to 4 described above. As may be taken from FIG. 9, a central processing unit (CPU) or image processor 51 is connected to a memory 52 for storing read-outs from the detectors or the finally reconstructed data. As indicated before, the data may be acquired by a CSCT scanner such as depicted in FIGS. 1 and 6. The image processor 51 may furthermore be connected to a plurality of input/output-network or other diagnosis devices via a connection 53. The image processor 51 is furthermore connected to a display 54 (for example, to a computer monitor) for displaying information or images computed or adapted in the image processor 51. An operator may interact with the image processor 51 via a keyboard 55 and/or other input or output devices, which are not depicted in FIG. 9.

The present invention described above, may, for example, be applied in the field of medical imaging. However, as described above, the present invention may also be applied in the field of non-destructive testing or baggage inspection.

We claim:

1. Data processing device for performing a reconstruction of computed x-ray tomography (CT) data, wherein the computed tomography data is reconstructed from acquired CT data, the data processing device comprising:
a detector comprising energy resolving detector elements configured to acquire at least a partial spectrum;
a memory configured to store at least one of the acquired CT data and the computed tomography data, and
a processor configured to perform at least the following operation:
determining a wave-vector transfer by using the at least partial spectrum;
determining a reconstruction volume,
wherein a dimension of the reconstruction volume is determined by the wave-vector transfer, wherein the wave-vector transfer represents curved lines in the reconstruction volume;
rendering the reconstruction volume; and
rearranging the acquired CT data such that it corresponds to an acquisition along a desired source trajectory in the reconstruction volume that is different than an actual source trajectory when the at least partial spectrum is acquired.

2. The data processing device of claim 1, wherein the acquired CT data is acquired during an acquisition wherein a source of radiation is displaced along a first source trajectory, wherein the acquired CT data are rearranged such that it corresponds to an acquisition along a second source trajectory in the reconstruction volume which is different than the first source trajectory, and wherein the first source trajectory is a circle and the second source trajectory is a helix.

3. The data processing device of claim 1, wherein the processor is configured to perform a filtered back-projection along the curved lines in the reconstruction volume.

4. The data processing device of claim 1, wherein the reconstruction volume is furthermore determined by two linear independent vectors of the rotation plane, and wherein the detector is a two dimensional detector.

5. The data processing device of claim 1, wherein the rearranging of the acquired CT data such that it corresponds to an acquisition along a helical source trajectory in the reconstruction volume is performed by using John's Equation.

6. The data processing device of claim 1, wherein the rearranging of the acquired CT data such that it corresponds to an acquisition along a helical source trajectory in the reconstruction volume is performed by using the following equation:

$$q = \tilde{q} + \frac{1}{2hc}\left[\frac{d_{min} + d_{max} - d}{d_{min} \times d_{max}}\right]\alpha E,$$

with q being the wave-vector transfer, $\tilde{q}$ being a virtual position of an x-ray source, h being the Planck's constant, c being the speed of light, $\alpha$ denoting an angular position of the x-ray source in the rotational plane, E being an energy of a corresponding x-ray photon, d denoting a distance from a scatter center of the corresponding x-ray photon from the detector and $d_{min}$ and $d_{max}$ being a beginning and an end of a region of interest of the curved lines in the reconstruction volume.

7. A computer x-ray tomography (CT) apparatus for examination of an object of interest, the computer tomography apparatus comprising: a detector unit with an x-ray source and a scatter radiation detector, wherein the detector unit is rotatable around a rotational axis extending through an examination area for receiving the object of interest, wherein the x-ray source generates a fan-shaped x-ray beam adapted to penetrate the object of interest in the examination area in a slice plane, wherein the scatter radiation detector is arranged at the detector unit opposite to the x-ray source with an offset with respect to the slice plane in a direction parallel to the rotational axis, wherein the scatter radiation detector includes a plurality of first detector elements, and wherein the plurality of first detector elements are energy-resolving detector elements; and a data processor which is adapted to perform at least the following operation: determining a wave-vector transfer by using the spectrum acquired by using the scatter radiation detector; determining a reconstruction volume, wherein a dimension of the reconstruction volume is determined by the wave-vector transfer, and wherein the wave-vector transfer represents curved lines in the reconstruction volume; and rearranging the acquired CT data such that it corresponds to an acquisition where the x-ray source is displaced along a desired source trajectory in the reconstruction volume that is different than an actual source trajectory when the spectrum is acquired.

8. The computer tomography apparatus of claim 7, wherein the scatter radiation detector is a two-dimensional detector.

9. The computer tomography apparatus of claim 7, wherein the scatter radiation detector is arranged at the detector unit opposite to the x-ray source parallel to the slice plane and out of the slice plane with such an offset along the rotational axis such that the scatter radiation detector is arranged for receiving a scatter radiation scattered from the object of interest, and wherein the acquired CT data is acquired during an acquisition wherein the x-ray source is displaced along a first source trajectory, wherein the acquired CT data are rearranged such that it corresponds to an acquisition along a second source trajectory in the reconstruction volume which is different to the first source trajectory, and wherein the first source trajectory is a circle and the second source trajectory is a helix.

10. The computer tomography apparatus of claim 7, wherein the acquired CT data is acquired during a circular acquisition wherein a source of radiation is rotated around an object of interest in a rotation plane, wherein the processor is furthermore adapted to perform a filtered back-projection along the curved lines in the reconstruction volume, and wherein the reconstruction volume is furthermore determined by two linear independent vectors of the rotation plane.

11. The computer tomography apparatus of claim 10, wherein the rearranging the acquired CT data such that it corresponds to an acquisition along a helical source trajectory in the reconstruction volume is performed by using the following equation:

$$q = \tilde{q} + \frac{1}{2hc}\left[\frac{d_{min} + d_{max} - d}{d_{min} \times d_{max}}\right]\alpha E,$$

with q being the wave-vector transfer, q̃ being a virtual position of the x-ray source, h being the Planck's constant, c being the speed of light, α denoting an angular position of the x-ray source in the rotational plane, E being an energy of a corresponding x-ray photon, d denoting a distance from a scatter center of the corresponding x-ray photon from a detector including the scatter radiation detector and $d_{min}$ and $d_{max}$ being a beginning and an end of a region of interest of the curved lines in the reconstruction volume.

12. Method of performing a reconstruction of computed x-ray tomography (CT) data, wherein the computed tomography data is reconstructed from acquired CT data comprising at least a partial spectrum acquired by using a detector comprising energy resolving detector elements, the method comprising acts of: determining a wave-vector transfer by using the at least partial spectrum; determining a reconstruction volume, wherein a dimension of the reconstruction volume is determined by the wave-vector transfer, and wherein the wave-vector transfer represents curved lines in the reconstruction volume; rendering the reconstruction volume; and rearranging the acquired CT data such it corresponds to an acquisition along a desired source trajectory in the reconstruction volume that is different than an actual source trajectory when the at least partial spectrum is acquired.

13. The method of claim 12, wherein the acquired CT data is acquired during an acquisition wherein a source of radiation is displaced along a first source trajectory, wherein the acquired CT data are rearranged such that it corresponds to an acquisition along a second source trajectory in the reconstruction volume which is different to the first source trajectory, wherein the first source trajectory is a circle and the second source trajectory is a helix, and wherein the detector is a two dimensional detector.

14. The method of claim 13, wherein the rearranging the acquired CT data such that they correspond to an acquisition along a helical source trajectory in the reconstruction volume is performed by using the following equation:

$$q = \tilde{q} + \frac{1}{2hc}\left[\frac{d_{min} + d_{max} - d}{d_{min} \times d_{max}}\right]\alpha E,$$

with q being the wave-vector transfer, q̃ being a virtual position of an x-ray source, h being the Planck's constant, c being the speed of light, α denoting an angular position of the x-ray source in the rotational plane, E being an energy of a corresponding x-ray photon, d denoting a distance from a scatter center of the corresponding x-ray photon from the detector and $d_{min}$ and $d_{max}$ being a beginning and an end of a region of interest of the curved lines in the reconstruction volume.

15. Computer program stored on a computer readable medium for a data processor for performing a reconstruction of computed x-ray tomography (CT) data, wherein the computed tomography data is reconstructed from acquired CT data comprising at least a partial spectrum acquired by using a detector comprising energy resolving detector elements, wherein the computer program causes the data processor to perform the following operations: determining a wave-vector transfer by using the at least partial spectrum; determining a reconstruction volume, wherein a dimension of the reconstruction volume is determined by the wave-vector transfer, and wherein the wave-vector transfer represents curved lines in the reconstruction volume; rearranging the acquired CT data such that they correspond to an acquisition along a desired source trajectory in the reconstruction volume that is different than the actual source trajectory when the at least partial spectrum is acquired; and rendering the reconstruction volume.

* * * * *